United States Patent [19]

Kita et al.

[11] Patent Number: 5,084,214

[45] Date of Patent: Jan. 28, 1992

[54] PHENOLIC THIOETHERS, AND THEIR PRODUCTION AND USE

[75] Inventors: Toru Kita; Shuh Narumiya, both of Kyoto; Masayuki Narisada, Ibaraki; Fumihiko Watanabe, Kitakatsuragi; Saichi Matsumoto, Ikeda; Masami Doteuchi, Hirakata, all of Japan

[73] Assignee: Shionogi & Co., Ltd., Osaka, Japan

[21] Appl. No.: 359,718

[22] Filed: May 31, 1989

[30] Foreign Application Priority Data

Jun. 24, 1988 [JP] Japan ................... 63-157849

[51] Int. Cl.$^5$ ............................................. C08H 03/00
[52] U.S. Cl. ................................. 260/399; 514/824; 568/38; 568/54; 568/67
[58] Field of Search ............... 568/38, 54, 67; 514/712, 824; 260/399

[56] References Cited

U.S. PATENT DOCUMENTS

| 4,012,523 | 3/1977 | Wagner .................. 514/570 |
| 4,076,841 | 2/1978 | Wagner, et al. ........ 514/570 |

FOREIGN PATENT DOCUMENTS

| 79855 | 5/1983 | European Pat. Off. .......... 568/54 |
| 0190682 | 8/1986 | European Pat. Off. . |
| 293895 | 12/1988 | European Pat. Off. .......... 568/54 |
| 1936463 | 2/1971 | Fed. Rep. of Germany . |
| 2406812 | 8/1974 | Fed. Rep. of Germany . |
| 63-310821 | 12/1988 | Japan . |

OTHER PUBLICATIONS

Tsuda et al., Chemical Abstracts, 90: 151802X, pg. 575, 1979.
Wagner et al., J. Medeanal Chemistry, vol 20, #8, 1977, pg. 1007-1013.
Chemical Abstracts, 85:14147V, p. 65, 1976.
Tsuda et al., Chemical Abstracts, 90: 1518024, p. 575, 1979.
Chemical Abstracts, vol. 94, No. 5, Feb. 2, 1981, Col. 30290 C.
Proc. Natl. Acad. Sci. U.S.A., vol. 85, pp. 2344–2348, Apr. 1988, Medical Sciences.
J. Clin. Invest., vol. 81, Mar. 1988, pp. 720–729.

*Primary Examiner*—Jose G. Dees
*Assistant Examiner*—Deborah D. Carr
*Attorney, Agent, or Firm*—Wenderoth, Lind & Ponack

[57] ABSTRACT

Phenolic thioethers of the formula:

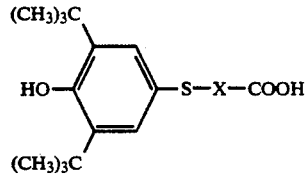

wherein R is a hydrogen atom or a protective group for carboxyl, X is a straight or branched $C_4$–$C_{15}$ alkylene group, a straight or branched $C_1$–$C_{15}$ alkylene group having a phenylene group or a straight or branched $C_2$–$C_{15}$ alkenylene group, and their salts, which inhibit the denaturation of low density lipoproteins (LDL) and the incorporation of LDL by macrophages and are useful as anti-arteriosclerosis agents.

15 Claims, No Drawings

PHENOLIC THIOETHERS, AND THEIR PRODUCTION AND USE

The present invention relates to phenolic thioethers, and their production and use. More particularly, it relates to novel phenolic thioethers, which inhibit the denaturation of low density lipoproteins (LDL) and the incorporation of LDL by macrophages and are useful as anti-arteriosclerosis agents, and their production and use.

Atherosclerosis is an extremely common form of arteriosclerosis in which deposits of yellowish plaques containing cholesterol, lipoid material and lipophages are formed within the intima and inner media of large and medium-sized arteries. As the factors causing atherosclerosis, there may be exemplified hypertension, hyperlipemia, excessive cigarette smoking, obesity, diabetes mellitus, hyperuricemia, stress, heredity, lack of exercise, etc., and the accumulation of two or more of these factors over a long period of time would lead to atherosclerosis. Among those factors, the behavior of cholesterol existing as LDL in blood is noted. The penetration of LDL into the arterial walls and the incorporation of LDL by macrophages, which produce the accumulation of cholesterol in the inner media and the troubles in the blood vessel, are especially important. On the other hand, the factors such as the increase of blood cholesterol due to the troubles on the incorporation of LDL into liver and the metabolism of LDL in liver, the hydrodynamic state of blood due to the change of the physical properties of blood and red blood corpuscles, the damage of endothelium, the abnormal hyperplasia of arterial walls and the depression of the lipid utilization in arterial tissues are considered to promote the occurrence of atherosclerosis.

For medical treatment of atherosclerosis, there have heretofore been used anti-arteriosclerosis agents such as pyridinol carbamate, lipid lowering agents such as chlofibrate, nicotinic acid, alpha-tyroxine and cholestyramine, anti-platelet agents such as dipyridamole and aspirin, etc. Also, di-tert-butylphenol derivatives having anti-arteriosclerosis activity are disclosed in JP-B-52027144, JP-B-60039262, JP-B-61026539, JP-A-52125171, etc. Further, structurally related compounds having antioxidative activity are disclosed in JP-A-49075551, JP-A-49075552, JP-A-58090545, JP-A-61191670, JP-A-61-197554, JP-A-61210073, JP-A-61218570, JP-A-61268664, U.S. Pat. No. 4,076,841, Chemical Abstracts, Vol. 94, 30290c (1981), etc.

It is generally considered that normal LDL are not incorporated by reticuloendothelial cells (scavenger cells) such as macrophages and Kupffer cells, but denaturated LDL are incorporated through a receptor thereto. Also, it is considered that the receptor for denatured LDL does not decrease in number even when a large amount of cholesterol is accumulated in cells so that the accumulation of cholesterol is remarkably increased, whereby the conversion into foam cells participating in the cause of atherosclerosis may take place.

According to the above considerations, atherosclerosis may be prevented by inhibiting the production of denatured LDL. Development of drugs which can inhibit the production of denatured LDL has thus been desired, but satisfaction is presently not obtained in this respect.

As the result of an extensive study, it has now been found that phenolic thioethers of the following formula and their salts are quite effective in inhibition of the denaturation of LDL:

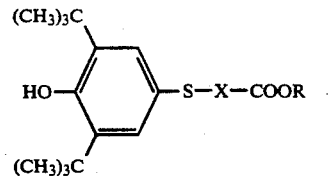

wherein R is a hydrogen atom or a protective group for carboxyl, X is a straight or branched $C_4$-$C_{15}$ alkylene group, a straight or branched $Cl$-$C_{15}$ alkylene group having a phenylene group or a straight or branched $C_2$-$C_{15}$ alkenylene group. (The term "alkenylene" as hereinabove used is intended to mean not only the one having only one double bond but also the one having two or more (particularly two) double bonds, inclusively.) Thus, they are useful for prevention of atherosclerosis.

With respect to the above formula (I), the protective group for carboxyl represented by the symbol R includes any carboxyl-protecting group having up to 19 carbon atoms, which is detachable without causing any undesirable change in any other portion of the molecule. Specifically, it includes a reactive carboxy-protecting group, a pharmaceutical carboxy-protecting group (i.e. pharmacologically active ester-forming group), etc.

Representative examples of the reactive carboxy-protecting group are an optionally substituted alkyl group having 1 to 8 carbon atoms (e.g. methyl, methoxymethyl, ethyl, ethoxymethyl, iodomethyl, propyl, isopropyl, butyl, isobutyl, ethoxyethyl, methylthioethyl, methanesulfonylethyl, trichloroethyl, t-butyl), an optionally substituted alkenyl group having 3 to 8 carbon atoms (e.g. propenyl, allyl, prenyl, hexenyl, phenylpropenyl, dimethylhexenyl), an optionally substituted aralkyl group having 7 to 19 carbon atoms (e.g. benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl), an optionally substituted aryl group having 6 to 12 carbon atoms (e.g. phenyl, tolyl, diisopropylphenyl, xylyl, trichlorophenyl, pentachlorophenyl, indanyl), an ester with an N-hydroxyamino compound having 1 to 12 carbon atoms (e.g. acetoxime, acetophenonoxime, acetoaldoxime, N-hydroxysuccinimide, N-hydroxyphthalimide), a hydrocarbonated silyl group having 3 to 12 carbon atoms (e.g. trimethylsilyl, dimethylmethoxysilyl, t-butyldimethylsilyl), a hydrocarbonated stannyl group having 3 to 12 carbon atoms (e.g. trimethylstannyl), etc. These groups may be further optionally substituted. Since the reactive carboxyl-protecting group is eliminated in an appropriate step up to the final target product, its structure is not important insofar as the purpose of protection is attained. Thus, various groups equivalent thereto (e.g. amide, acid anhydride with a carbonic acid or a carboxylic acid) may be used.

The pharmaceutical carboxyl-protecting group may be, for instance, a pharmacologically active ester-forming group such as an ester-forming group showing an inhibitory activity on the incorporation by macrophages, a lipid-oxidation preventing activity or an ulcer controlling activity on the oral or parenteral administration. Representative examples are a 1-oxygen-substituted alkyl group having 2 to 15 carbon atoms such as straight, branched, cyclic or partially cyclic alkanoyloxyalkyl (e.g. acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl), alkoxycarbonyloxyalkyl having 3 to 15 carbon atoms (e.g. ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl), alkoxyalkyl having 2 to 8 carbon atoms (e.g. methoxymethyl, methoxyethyl), 2-oxacycloalkyl having 4 to 8 carbon atoms (e.g. tetrahydropyranyl, tetrahydrofuranyl ester), substituted aralkyl having 8 to 12 carbon atoms (e.g. phenacyl, phthalidyl), aryl having 6 to 12 carbon atoms (e.g. phenyl, xylyl, indanyl), alkenyl having 2 to 12 carbon atoms (e.g. allyl, (2-oxo-1,3-dioxolyl)methyl), etc. These groups may further be optionally substituted.

Examples of the straight or branched $C_4$-$C_{15}$ alkylene group represented by the symbol X (as having a carboxyl group at the 1-position) may be tetramethylene, pentamethylene, hexamethylene, heptamethylene, octamethylene, nonamethylene, decamethylene, undecamethylene, dodecamethylene, tridecamethylene, tetradecamethylene, pentadecamethylene, 1,1-dimethylethylene, 2,2-dimethylethylene, 1-methyltrimethylene, 1-ethyltrimethylene, 2-methyltrimethylene, 2,2-dimethyltrimethylene, 1-methyltetramethylene, 2-methyltetramethylene, 2,2-dimethylhexamethylene, 1-methylheptamethylene, 2-methylheptamethylene, 2,2-dimethylheptamethylene, 1-methyloctamethylene, 2-methyloctamethylene, 2,2-dimethyloctamethylene, 2-methylnonamethylene, 2,2-dimethylnonamethylene, etc.

As the straight or branched $C_2$-$C_{15}$ alkenylene group represented by X (as having a carboxyl group at the 1-position), there may be exemplified vinylene, 1-propene-1,3-diyl, 2-methyl-1-propene-1,3-diyl, 2-methyl-1-propene-1,2-diyl, 1-butene-1,4-diyl, 1,3-butadiene-1,4-diyl, 1-butene-1,3-diyl, 1-pentene-1,5-diyl, 1,3-pentadiene-1,5-diyl, 1-hexene-1,6-diyl, 1,3-hexadiene-1,6-diyl, 1-heptene-1,7-diyl, 2,6-dimethyl-1,5-heptadiene-1,6-diyl, 1,3,5-heptatrilene-1,7-diyl, 2,6-dimethyl-1,3,5-heptatriene-1,6-diyl, 1-octene-1,8-diyl, 1,3-octadiene-1,8-diyl, 1-nonene-1,9-diyl, 1-decene-1,10-diyl, 1-undecene-1,11-diyl, 1-dodecene-1,12-diyl, 1-tridecene-1,13-diyl, 1-tetradecene-1,14-diyl, 1-pentadecene-1,15-diyl, 1-methyl-2-butene-1,3-diyl, 2-butene-2,3-diyl, 4-methyl-1-pentene-1,5-diyl, 1-hexene-1,4-diyl, 6-methyl-1-heptene-1,7-diyl, 1-octene-1,7-diyl, 7-methyl-1-nonene-1,9-diyl, 8,8-dimethyl-1-decene-1,10-diyl, etc.

Examples of the straight or branched C -$C_{15}$ alkylene group having a phenylene group represented by X are those having a $C_1$-$C_{15}$ alkylene group (e.g. methylene, ethylene, trimethylene) or a $C_4$-$C_{15}$ alkylene group at the 4-position of a phenyl group (as having a carboxyl group at the 1-position), optionally further bonded with a $C_1$-$C_{15}$ alkylene group at the 1-position.

When X in the phenolic thioethers (I) represents a hydrogen atom, it may be in the form of a free acid or a salt. In case of a salt form, it may be in a metal salt form or a quaternary ammonium salt form. Examples of the metal which forms a metal salt are metals belonging to Groups I to III in the 2nd to 4th period in the periodic table (e.g. lithium, sodium, potassium, magnesium, calcium, aluminium). Examples of the amine which forms a quaternary ammonium salt are alkylamines having not more than 12 carbon atoms (e.g. trimethylamine, triethylamine, methylmorpholine), aromatic bases having not more than 9 carbon atoms (e.g. pyridine, collidine, picoline, quinoline, dimethylaniline), amino acids (e.g. glycine, lysine, arginine), etc. The quaternary ammonium salt is suitable for production or storage.

Illustrative examples of the phenolic thioethers (I) of the invention are as follows:

5-(3,5-Di-tert-butyl-4-hydroxyphenylthio)pentanoic acid;

6-(3,5-Di-tert-butyl-4-hydroxyphenylthio)hexanoic acid;

7-(3,5-Di-tert-butyl-4-hydroxyphenylthio)heptanoic acid;

11-(3,5-Di-tert-butyl-4-hydroxyphenylthio)undecanoic acid;

12-(3,5-Di-tert-butyl-4-hydroxyphenylthio)-dodecanoic acid;

3-(3,5-Di-tert-butyl-4-hydroxyphenylthio)acrylic acid;

6-(3,5-Di-tert-butyl-4-hydroxyphenylthio)-2,4-hexadienoic acid;

4-(3,5-Di-tert-butyl-4-hydroxyphenylthio)crotonic acid;

alpha-(3,5-Di-tert-butyl-4-hydroxyphenylthio)-p-toluic acid, etc.

These compounds can be converted into their salts or esters, when desired.

The phenolic thioethers (I) can be produced by reacting 2,6-di-tert-butyl-4-mercaptophenol of the formula:

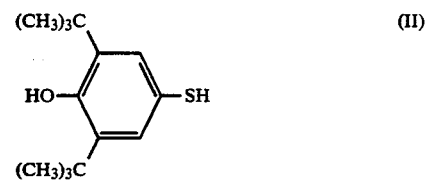

(JP-A-61-268664) with an alkylating agent, optionally followed by carboxyl-protecting group formation, salt-formation and/or carboxy-protecting group elimination.

The reaction may be performed in a per se conventional procedure for synthesis of a sulfide. As the alkylating agent, there may be exemplified (A) halogenated aliphatic acids such as (1) halogenated alkanoic acids (e.g. 4-bromobutanoic acid, 5-bromopentanoic acid, 6-bromohexanoic acid, 6-bromo-3-methylhexanoic acid, 7-bromoheptanoic acid, 8-bromooctanoic acid, 9-bromononanoic acid, 10-bromodecanoic acid, 11-bromoundecanoic acid, 12-bromodecanoic acid, 13-bromotridecanoic acid, 14-bromotetradecanoic acid, 15-bromopentadecanoic acid, their 2-methyl, 2,2-dimethyl and/or chloro derivatives), (2) halogenated alkenoic acids (e.g. 2-bromo-2-propenoic acid, 4-bromo-2-butenoic acid, 5-bromo-2-pentenoic acid, 6-bromo-2-hexanoic acid, 6-bromo-2,4-hexanedienoic acid, 7-bromo-2-heptenoic acid, 7-bromo-2,4-heptadienoic acid, 8-bromo-2-octenoic acid, 8-bromo-4-octenoic acid, 8-bromo-2,4-octadienoic acid, 8-bromo-2,4,6-octatrienoic acid, 9-bromo-2-noneic acid, 10-bromo-2,4-decadienoic acid) or (3) halogenated alkanoic acids having a phenylene group (e.g. alpha-bromo-p-toluic acid, 4-bromomethylphenylacetic acid), (B) unsaturated aliphatic acids such as (1) alkenoic acid (e.g 2-butenoic acid, 4-hentenoic acid, 5-hexanoic acid, 6-heptenoic acid, 7-octenoic acid, 8-nonenonic acid, 9-decenoic acid, 10-undecenoic acid, 11-decenoic acid, 12-tridecenoic acid, 13-tetradecenoic acid, 14-pentadecenoic acid, 2,5-hexadienoic acid) or (2) alkynoic acid (e.g. 2-propionic acid, 2-butynic acid) and their carboxy-protected derivatives, for instance, carboxylic esters.

When a halogenated aliphatic acid is used as the alkylating agent, the reaction may be carried out in the presence of a base (e.g. sodium hydroxide, potassium hydroxide, calcium hydroxide, potassium carbonate, pyridine, triethylamine) in a solvent such as alcohols (e.g. methanol, ethanol, propanol, t-butanol), ethers (e.g. diethyl ether, tetrahydrofuran), aromatic solvents (e.g. benzene) and N,N-dimethylacetamide under cooling, at room temperature or while reflux for a period of about 10 minutes to several ten hours. For acceleration of the reaction, the reaction may be carried out in a heterogeneous phase of an organic layer and an aqueous layer in the presence of a phase transfer catalyst (e.g. hexadodecyl-tri-n-butylphosphonium bromide, tetraethylammonium chloride).

When an unsaturated aliphatic acid is used as the alkylating agent, the reaction is normally effected in an ethereal solvent (e.g. diethyl ether, tetrahydrofuran) at room temperature or under heating, if necessary, in the presence of an activator such as oxygen, peroxides, azobisisobutyronitrile, sulfur, sulfuric acid, piperidine, triethylamine, Triton B ® or N-methylmorpholine.

Elimination of the carboxyl-protecting group may be accomplished by a per se conventional procedure, for instance, by treating with water in a water-miscible solvent such as an alcohol (e.g. methanol, ethanol), an ether (e.g. diethyl ether, tetrahydrofuran, dioxane) or 1,2-dimethoxyethane, if necessary, in the presence of an acidic catalyst (e.g. hydrochloric acid, sulfuric acid, phosphoric acid, acetic acid, p-toluenesulfonic acid, methanesulfonic acid) or a basic catalyst (e.g. sodium hydroxide, potassium hydroxide, sodium hydrogencarbonate, sodium methoxide) at room temperature or under heating for a period of several minutes to several hours, or by catalytic reduction.

The active ester-formation may be achieved by a per se conventional procedure, for instance, by reacting the phenolic thioether (I: R =H) with an alcohol or phenol derivative in the presence of a condensing agent such as dicyclohexylcarbodiimide, by reacting the acid chloride derivative of said phenolic thioether with an alcohol or phenol derivative in the presence of a basic substance (e.g. metallic magnesium, dimethylaniline, pyridine, sodium hydroxide), by reacting said phenolic thioether with an alcohol or phenol derivative in the presence of an acid catalyst (e.g. dry hydrogen chloride, conc. sulfuric acid), or by reacting a salt of said phenolic thioether with a halide.

The salt of the phenolic thioether (I: R=H) as above stated can be easily produced according to a per se conventional procedure, for instance, by reacting the phenolic thioether with an appropriate base such as an alkali metal or alkaline earth metal hydroxide or carbonate, ammonium hydroxide, ammonia or an organic amine in a theoretical amount in an appropriate solvent. The salt is readily recovered from the reaction mixture, for instance, by lyophylizing or concentrating and filtering.

The phenolic thioethers (I) of the invention can prevent the incorporation of LDL into macrophages, the oxidation of lipid, the formation of ulcer, etc. Therefore, they are useful for prevention and treatment of arteriosclerosis, gastric ulcer, allergic diseases, phlogistic symptoms, etc.

The phenolic thioethers (I) may be administered orally or parenterally to patients. For the oral administration, they are normally formulated into conventional preparation forms such as solid preparations (e.g. tablets, powders, capsules, granules) or liquid preparations (e.g. aqueous dispersions, oily suspensions, syrups, elixirs). For the parenteral administration, they are usually applied in an injectable form such as aqueous solutions or oily dispersions. On the formulation of the above preparations, there may be used excipients, binding agents, lubricants, solvents, solubilizers, emulsifiers, dispersants, etc. Other additives such as preservatives and stabilizing agents may be also used.

The dosage of the phenolic thioethers (I) varies depending upon the dosage form, age, bodyweight, symptom, etc. of the patient. For instance, the dosage for an adult ranges usually from about 5 to 5000 mg per day for oral administration or 0.5 mg to 500 mg per day for subcutaneous injection.

Practical and presently preferred embodiments for production of the phenolic thioethers (I) are shown in the following Examples, but it should be understood that these examples are given only for the illustrative purposes and do not limit the present invention thereto.

EXAMPLE 1

5-(3,5-Di-tert-butyl-4-hydroxyphenylthio)pentanoic acid (Ia):

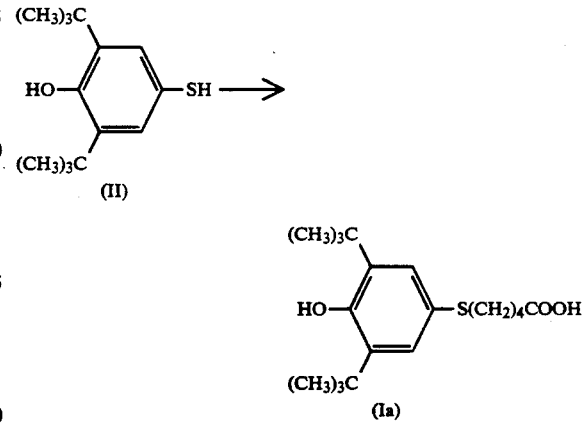

To a solution of 2,6-di-tert-butyl-4-mercaptophenol (II) (400 mg) in ethanol (4 ml), a solution of sodium hydroxide (134 mg; 2 equivalents) in water (0.3 ml) was added while cooling with ice in nitrogen stream, and the resultant mixture was kept at the same temperature for 5 minutes. After addition of 5-bromopentanoic acid (334 mg; 1 equivalent) thereto, the resulting mixture was stirred for 1 hour and allowed to stand at room temperature overnight. The reaction mixture was poured into water, made acidic with 2N hydrochloric acid in the presence of ethyl acetate and extracted with ethyl acetate. The organic layer was washed with water, dried over magnesium sulfate and concentrated under reduced pressure to give an oily residue, which was chromatographed on silica gel and eluted with a mixture of toluene and ethyl acetate (9 : 1 to 2 : 1 by volume) to give an oily residue (555 mg). Recrystallization from a mixture of ethyl ether and n-hexane gave the objective compound (Ia) (423 mg). m.p., 99 - 100° C. Yield, 74.4 %.

Elementary analysis ($C_{19}H_{30}O_3S$: 338.50):

Calcd. (%): C, 67.41; H, 8.93; S, 9.47.

Found (%): C, 67.40; H, 8.79, S, 9.32.

IR $\nu$ max (CHCl$_3$) cm 3640, 3520, 3040 (br), 1740, 1710.

NMR $\delta$ ppm (CDCl$_3$) 1.45 (s, 18H), 1.60-1.90 (m, 4H), 2.28-2.44 (m, 2H), 2.75-2.90 (m, 2H), 5.17 (s, 1H), 7.23 (s, 2H).

EXAMPLES 2 to 4

3,5-Di-tert-butyl-4-hydroxyphenylthioalkanoic acid (Ib - Id):

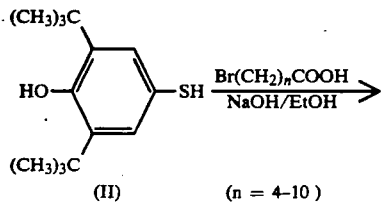

(n = 4-10)

residue was chromatographed on silica gel and eluted with a mixture of toluene and ethyl acetate (9 : 1 to 2 : 1 by volume). The collected fractions were concentrated under reduced pressure. The crystalline residue was recrystallized from n-hexane to give the objective compound (Ib - Id). According to the above general procedure, the reaction was conducted under the conditions as shown in Table 1 to give the products as shown below and in Table 2. 6-(3,5-Di-tert-butyl-4-hydroxyphenylthio)hexanoic acid (Ib);

7-(3,5-Di-tert-butyl-4-hydroxyphenylthio)heptanoic acid (Ic);

11-(3,5-Di-tert-butyl-4-hydroxyphenylthio)undecanoic acid (Id).

TABLE 1

| Example No. | n | 2,6-di-tert-butyl-4-mercaptophenol (II) (g) | Ethanol (ml) | 5N NaOH (ml) | Bromo-alkanoic acid (g) |
|---|---|---|---|---|---|
| 2 | 5 | 2.0 | 18 | 3.36 | 1.63 |
| 3 | 6 | 2.0 | 18 | 3.36 | 1.75 |
| 4 | 10 | 0.6 | 6 | 1 | 0.33 |

TABLE 2

| Example No. | n | Objective compound (I) | Yield (%) | Melting point (°C.) | $^1$H-NMR $\delta$ ppm (CDCl$_3$) | IR $\nu$ max (CHCL$_3$) | Elementary analysis (%) |
|---|---|---|---|---|---|---|---|
| 2 | 5 | (Ib): 1st Crystal 1.75 g 2nd Crystal 0.4 g | 72.7 | 1st Crystal 57–57.5 2nd Crystal 55–56 | 1.37–1.75 (m,24H), 2.27–2.40 (m,2H), 2.74–2.89 (m,3H), 5.16 (s,1H), 7.25 (s,2H) 9.3–10.5 (br, 1H) | 3640, 3520, 3040br, 1745, 1711 | for $C_{20}H_{32}O_3S$ Calcd.: C, 68.13 H, 9.15 S, 9.10 Found: C, 68.07 H, 9.12 S, 9.24 |
| 3 | 6 | (Ic): 1st Crystal 1.38 g 2nd Crystal 0.78 g | 70.2 | 1st Crystal 52.3–53 2nd Crystal 50–51 | 1.20–1.82 (m,26H), 2.34 (t,J=7Hz,2H), 2.82 (t,J=7Hz,2H), 5.17 (s,1H), 7.25 (s,2H) 10.88 (br, 1H) | 3640, 3520, 3040br, 1740, 1710.5 | for $C_{21}H_{34}O_3S$ Calcd.: C, 68.81 H, 9.35 S, 8.75 Found: C, 68.59 H, 9.37 S, 8.62 |
| 4 | 10 | (Id): 0.248 g | 47.3* | 40–41 | 1.25 (s,18H), 1.40–1.80 (m,16H), 2.34 (t,J=7Hz,2H), 2.82 (t,J=7Hz,2H), 5.16 (s,1H), 7.22 (s,2H) | 3642, 3520, 3040br, 1743, 1711 | for $C_{25}H_{42}O_3S$ Calcd.: C, 71.04 H, 10.02 S, 7.59 Found: C, 70.88 H, 9.96 S, 7.42 |

Note: *Calculated on the basis of 11-bromoundecanoic acid.

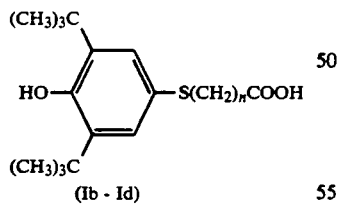

(Ib - Id)

To a solution of 2,6-di-tert-butyl-4-mercaptophenol (II) in ethanol, 5N sodium hydroxide solution (see Table 1) was added while cooling with ice in nitrogen stream, and the resultant mixture was kept at the same temperature for 5 minutes. After addition of bromoalkanoic acid thereto, the resulting mixture was stirred for 1 hour and allowed to stand at room temperature overnight. The reaction mixture was poured into water, made acidic with 2N hydrochloric acid in the presence of ethyl acetate and extracted with ethyl acetate. The organic layer was washed with water, dried over magnesium sulfate and concentrated under reduced pressure. The

EXAMPLE 5

12-(3,5-Di-tert-butyl-4-hydroxyphenylthio)dodecanoic acid (Ie):

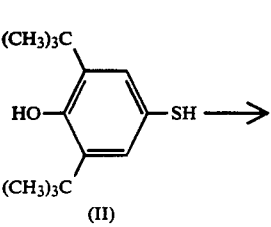

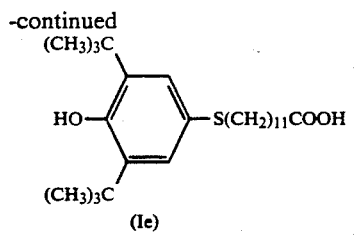

To a solution of 2,6-di-tert-butyl-4-mercaptophenol (II) (477 mg; 2 mmol) in dry ethanol (20 ml), water containing 12-bromododecanoic acid (558 mg; 2 mmol) and 97 % sodium hydroxide (250 mg; 6 mmol) was added, and the resultant mixture was allowed to stand at room temperature for 20 hours. The reaction mixture was made acidic with 10 aqueous acetic acid and extracted with ethyl acetate. The extract was washed two times with water, dried over anhydrous sodium sulfate and concentrated under reduced pressure. The crude product thus obtained was chromatographed on silica gel and eluted with ethyl acetate. The collected fractions were concentrated under reduced pressure. The residue was recrystallized from a mixture of water and methanol (1 : 1 by volume) to give the objective compound (Ie) (680 mg). Yield, 78 %. m.p., 41°-42° C.

Elementary analysis ($C_{26}H_{44}O_3S$):
Calcd. (%): C, 71.51; H, 10.16; S, 7.34.
Found (%): C, 71.15; H, 10.32; S, 7.13.
IR $\nu$ max (Nujol) cm-1 3640 (OH), 1720, 1695 (CO).
NMR $\delta$ ppm (CDCl$_3$): 1.25 (s, 18H, 16×CH$_2$), 1.42 (s, 18H, 2×C(CH$_3$)$_3$, 1.60 (m, 2H, —CH$_2$,CH$_2$CO—) 2.31 (t, 2H, CH$_2$CO), 2.80 (t, 2H, —SCH$_2$—), 5.22 (s, 1H, OH), 7.20 (s, 2H, aromatic H).

EXAMPLE 6

3-(3,5-Di-tert-butyl-4-hydroxy)phenylthioacrylic acid (If):

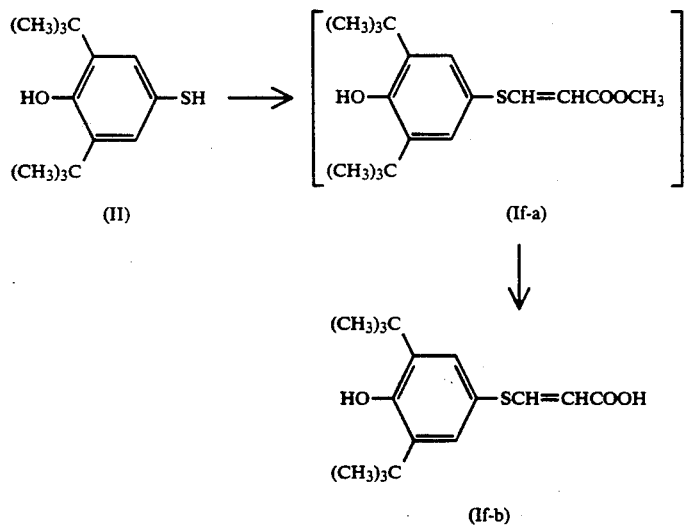

To a solution of 2,6-di-tert-butyl-4-mercaptophenol (II) (980 mg; 4.11 mmol) in dry tetrahydrofuran (20 ml), methyl propiolate (360 mg; 4.3 mmol) and N-methylmorpholine (435 mg; 4.3 mmol) were added, followed by heating under reflux for 3 hours. The reaction mixture was concentrated under reduced pressure and extracted with ethyl acetate (100 ml). The extract was washed with water (100 ml) two times and concentrated under reduced pressure to give an intermediate ester as colorless crystals (If-a) (1.28 g). Yield, 96.6 %. m.p., 102°-103° C. The intermediate ester (1.28 g) was dissolved in ethanol (50 ml), 10 sodium hydroxide solution (20 ml) was added thereto, and the resultant mixture was allowed to stand at room temperature for 20 hours. To the reaction mixture, acetic acid (2 ml) was added, and the resulting mixture was concentrated under reduced pressure. The oily substance as precipitated was extracted with ethyl acetate (50 ml). The extract was washed with water (50 ml) two times, dried over anhydrous sodium sulfate and concentrated under reduced pressure. The crystalline residue was recrystallized from a mixture of water and methanol (1 : 1 by volume) to give the objective compound (If-b) (890 mg). Yield, 70 %. m.p., 217°-219° C.

Elementary analysis ($C_{17}H_{24}O_3S$):
Calcd. (%): C, 66.20; H, 7.84; S, 10.39.
Found (%): C, 65.85; H, 7.82; S, 10.24.
IR $\nu$ max (Nujol) cm$^{-1}$: 3630 (OH), 1692, 1670 (CO).
NMR $\delta$ ppm (CDCl$_3$): 1.45 (s, 18H, 2×C(CH$_3$)$_3$, 5.42 (s, 1H, OH), 5.52 (d, 1H, J=15 Hz, =CH—CO), 7.26 (s, 2H, 2×aromatic H), 7.89 (d, 1H, J=15 Hz, —S—CH=).

EXAMPLE 7

6-(3,5-Di-tert-butyl-4-hydroxyphenylthio)-2,4-hexadienoic acid (Ig):

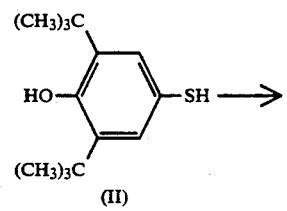

-continued

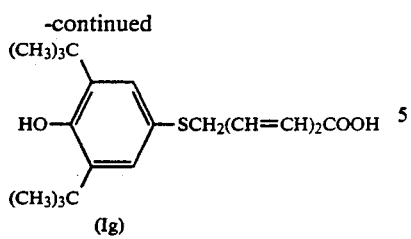

(Ig)

To a solution of 2,6-di-tert-butyl-4-mercaptophenol (II) (238 mg; 1 mmol) in dry ether (5 ml), triethylamine (150 μl) was added, and a solution of methyl 6-bromo-2,4-hexadienoate (205 mg; 1 mmol) in dry ether (2 ml) was added thereto while cooling with ice. The reaction mixture was stirred at room temperature for 2 hours, combined with water (20 ml) and extracted with ether (50 ml). The extract was washed with water (50 ml) two times, dried over anhydrous sodium sulfate and concentrated under reduced pressure. The oily residue was chromatographed on silica gel and eluted with a mixture of ether and n-hexane (1 : 2 by volume). The intermediate product (380 mg) thus obtained was dissolved in ethanol (20 ml), 5 % aqueous sodium hydroxide solution (5 ml) was added thereto, and the resultant mixture was allowed to stand at room temperature for 20 hours. To the reaction mixture, acetic acid (1 ml) was added, and the ethanol was evaporated under reduced pressure to make a volume of about 5 ml. The condensate was extracted with ethyl acetate (50 ml), and the extract was washed with water (50 ml) two times, dried over anhydrous sodium sulfate and concentrated under reduced pressure. The residue was chromatographed on silica gel and eluted with a mixture of ethyl acetate and methanol (10 : 1 by volume). The collected fractions were concentrated under reduced pressure, and the crystalline residue was recrystallized from a mixture of ether and n-hexane (1 : 4 by volume) to give the objective compound (Ig) (105 mg). m.p., 129°–131° C. Yield, 30 %.

Elementary analysis ($C_{20}H_{28}O_3S$):
Calcd. (%): C, 68.93; H, 8.10; S, 9.20.
Found (%): C, 68.84; H, 8.07; S, 9.06.
IR $\nu$max (Nujol) cm$^{-1}$: 3640 (OH), 1690, 1675 (CO).
NMR δ ppm (CDCl$_3$) 1.40 (s, 18H, 2×C(CH$_3$)$_3$), 3.49 (d, 2H, J=7 Hz, SCH ), 5.25 (s, 1H, OH), 5.65–6.39 (m, 4H, —CH=CH—CH=CH—), 7.22 (s, 2H, 2×aromatic H), 9.20 (broad, 1H, COOH).

EXAMPLE 8

4-(3,5-Di-tert-butyl-4-hydroxyphenylthio)crotonic acid (Ih):

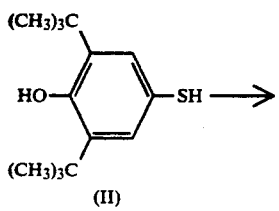

(II)

-continued

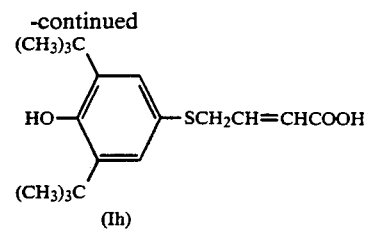

(Ih)

To a solution of 2,6-di-tert-butyl-4-mercaptophenol (II) (590 mg; 2.48 mmol) in dry ether (10 ml), triethylamine (303 mg; 3 mmol) was added, and a solution of ethyl 4-bromocrotonate (580 mg; 3 mmol) in dry ether (5 ml) was added while cooling with ice, followed by stirring at room temperature for 2 hours. The reaction mixture was combined with water (50 ml) and extracted with ether (50 ml). The extract was washed with water (50 ml) two times and concentrated under reduced pressure. The crude intermediate product as pale yellow oil was dissolved in ethanol (30 ml), 10 % sodium hydroxide solution (3 ml) was added thereto, and the resultant mixture was stirred at room temperature for 2 hours. To the reaction mixture, acetic acid (2 ml) was added, and the resulting mixture was concentrated under reduced pressure to make a volume of about 10 ml, which was extracted with ethyl acetate (50 ml). The extract was washed with water (50 ml) two times, dried over anhydrous sodium sulfate and concentrated under reduced pressure. The residual oil was chromatographed on silica gel and eluted with ethyl acetate. The collected fractions were concentrated under reduced pressure, and the crystalline residue was recrystallized from n-pentane to give the objective compound (Ih) (270 mg). m.p., 104°–106° C. Yield, 34 %.

Elementary analysis ($C_{18}H_{26}O_3S$):
Calcd. (%): C, 67.05; H, 8.13; S, 9.94.
Found (%): C, 66.99; H, 8.11; S, 10.04.
IR $\nu$ max (Nujol) cm$^{-1}$: 3640 (OH), 1713, 1705 (CO).
NMR δ ppm (CDCl$_3$) 1.43 (s, 18H, 2×C(CH$_3$)$_3$), 3.34 (d, 2H, J=6 Hz, —SCH$_2$—), 5.26 (s, 1H, OH), 5.75 (d, t, 1H, J=15 Hz and 6 Hz, —CH$_2$CH=), 6.30 (d, 1H, J=15 Hz, =CHCO), 7.22 (s, 2H, 2×aromatic H).

EXAMPLE 9 alpha-(3,5-Di-tert-butyl-4-hydroxyphenylthio)-p-toluic acid (Ii):

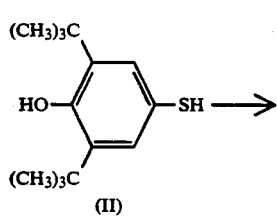

(II)

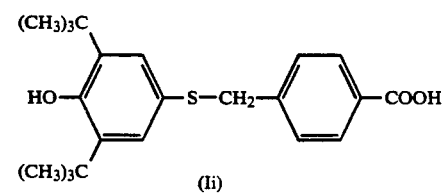

(Ii)

To a solution of 2,6-di-tert-butyl-4-mercaptophenol (II) (500 mg) in ethanol (5 ml), 5N sodium hydroxide solution (0.83 ml) was added while cooling with ice in nitrogen stream, and the resultant mixture was kept at the same temperature for 3 minutes. After addition of alpha-bromo-p-toluic acid (451 mg) thereto, the reaction mixture was stirred for 1 hour, poured into water and made acidic with 2N hydrochloric acid in the presence of ethyl acetate, followed by extraction with ethyl acetate. The extract was washed with water, dried over magnesium sulfate and concentrated under reduced pressure. The residue was chromatographed on silica gel and eluted with a mixture of n-hexane and ethyl acetate (9 : 1 to 2 : 1 by volume). The collected fractions were concentrated under reduced pressure, and the crystalline residue (655 mg) was recrystallized from a mixture of ethyl ether and n-hexane to give the objective compound (Ii) (620 mg). m.p., 177 - 179° C. Yield, 79.3 %.

Elementary analysis ($C_{22}H_{28}O_3S$):
Calcd. (%): C, 70.93; H, 7.58; S, 8.61.
Found (%): C, 70.97; H, 7.52; S, 8.43.

IR $\nu$ max ($CHCl_3$) cm 3640, 3525, 3015 (br), 1733, 1695, 1611, 1578.

NMR $\delta$ ppm ($CDCl_3$) 1.35 (s, 18H), 3.97 (s, 2H), 5.22 (s, 1H), 7.07 (s, 2H), 7.23 (2H, $A_2B_2q$-A part J=8Hz), 8.00 (2H, $A_2B_2q$-B part J=8Hz).

The pharmacological activities of some of the compounds (I) are illustratively shown in the following Test Examples.

TEST EXAMPLE 1

Activity of the suppression on the oxidation of LDL by $Cu^{2+}$, forming denatured LDL:

The suppressive activity was evaluated by (1) the suppression of the increase in the formation of thiobarbituric acid-reactive substance (TBA reactive substance) and (2) the suppression of incorporation of cupric ion oxidized LDL by macrophage measured as the amount of incorporated $^{14}$C-oleic acid as its cholesteryl ester. The observation was carried out in the manner as set forth below according to the disclosure in Yokode et al.: Journal of Clinical Investigation (J.Clin.Invest.), 81, 720–729, 1988).

The test compound was dissolved in dimethyl sulfoxide (DMSO) to make a concentration of 250 mM and diluted with ethanol to make a final concentration of 2 mM. For comparison, 2,6-di-tert-butyl-4-methylphenol (BHT) was dissolved in ethanol to make a final concentration of 2 mM.

Separately, human LDL was suspended in a 5 $\mu M$ copper sulfate solution (II), prepared by the Yokode et al method, to make a concentration of 0.36 mg/ml. To 1 ml of the suspension, 10 $\mu l$ of the test compound solution were incubation at 37° C. for 24 hours in the presence of $^{14}$C-oleic acid.

(1) Quantitative analysis of peroxidized lipid (TBA reactive substance):

Said incubated solution was subjected to measurement of the amount of peroxidized lipid as the amount of malondialdehyde estimated from the amount of the TBA reactive substance. Namely, the TBA reactive substance in the supernatant of the incubated solution after removal of proteins therefrom was measured by the TBA method. The results are shown in Table 3.

TABLE 3

| Test compound | TBA reactive substance (nmol malondialdehyde/mg protein) |
|---|---|
| Ib | 27.8 |

TABLE 3-continued

| Test compound | TBA reactive substance (nmol malondialdehyde/mg protein) |
|---|---|
| BHT | 31.9 |
| Control | 48.6 |

(2) Activity of the suppression on the incorporation of LDL by macrophages:

Said incubated solution was combined with macrophages to make a concentration of 60 $\mu g/ml$ in terms of proteins and incubated in a $CO_2$ incubator at 37° C. for 6 hours in the presence of $^{14}$C-labeled oleic acid. The amount of LDL taken into macrophages was determined as the amount of the incorporated $^{14}$C-oleic acid into macrophages as its cholesteryl ester. The results are shown in Table 4.

TABLE 4

| Test compound | Cholesteryl.[$^{14}$C]oleate (nmol/mg of cell protein/6 hrs) |
|---|---|
| Ib | 0.52 |
| BHT | 0.24 |
| Control | 3.18 |

As understood from Tables 3 and 4 above, the compounds (I) exert remarkable suppression on the production of peroxidized lipid by oxidation of LDL and also prevent the accumulation of cholesteryl ester in macrophages.

TEST EXAMPLE 2

Suppression on production of peroxidized lipid in a homogenate of rat brain:

SD strain rats (body weight, about 200 g) were sacrificed by cutting their heads, and the brains were taken out. The brains were homogenated with a 4 time amount of 0.05 M phosphate-sodium chloride buffer (pH, 7.4) and centrifuged at 1,000 g for 10 minutes. The supernatant was kept at -80° C. for storage.

The supernatant was diluted with a 2 time amount of the same phosphate-sodium chloride buffer as above, and 0.48 ml of the dilution was combined with ethanol as a vehicle or the test compound (30 $\mu l$), followed by incubation at 37° C. for 30 minutes. The reaction was interrupted by addition of 0.1 % butylhydroxytoluene (BHT) in ethanol (20 $\mu l$) and 25 % metaphosphoric acid (125 $\mu l$) and subjected to elimination of proteins. The per ⓒxidized lipid in the supernatant was measured by the thiobarbituric acid (TBA) method according to the description in Ohkawa et al: Anal. Biochem., Vol. 95, page 351 (1979). The produced amount of peroxidized lipid measured as TBA reactive substance was compared with that in the ethanol-added group and expressed in % control. The results are shown in Table 5.

TABLE 5

| Test compound | Final concentration (mM) | Peroxidized Lipid produced (expressed in % to control) |
|---|---|---|
| Ia | 0.001 | 86.7 |
|  | 0.01 | 22.5 |
|  | 0.1 | 6.9 |
| Ib | 0.001 | 78.8 |
|  | 0.01 | 6.1 |
|  | 0.1 | 0 |
| Ic | 0.001 | 87.3 |

TABLE 5-continued

| Test compound | Final concentration (mM) | Peroxidized Lipid produced (expressed in % to control) |
| --- | --- | --- |
| | 0.01 | 24.9 |
| | 0.1 | 6.4 |
| Id | 0.001 | 87.9 |
| | 0.01 | 19.1 |
| | 0.1 | 3.8 |
| Ie | 0.001 | 85.5 |
| | 0.01 | 22.5 |
| | 0.1 | 6.4 |
| If-b | 0.001 | 96.8 |
| | 0.01 | 72.8 |
| | 0.1 | 10.3 |
| Ih | 0.001 | 97.4 |
| | 0.01 | 39.3 |
| | 0.1 | 6.6 |
| Ii | 0.001 | 93.4 |
| | 0.01 | 28.5 |
| | 0.1 | 5.3 |
| Probucol* | 0.001 | 102.4 |
| | 0.01 | 58.3 |
| | 0.1 | 27.8 |

Note: *Commercially available (Merck Index (10th Ed.) 7657).

It is understood from Table 5 above, the compounds (I) according to the invention show an excellent antioxidation activity to lipids and can be expected to inhibit the formation of atheroma as the initial process for arteriosclerosis. Thus, they would be useful as antisclerosis drugs.

Besides, the compounds (I) are expected to show prevention on the incorporation of denatured LDL by macrophages due to cigarette smoking.

What is claimed is:

1. A phenolic thioether of the formula $$\text{(CH}_3\text{)}_3\text{C} - \text{HO} - \text{C}_6\text{H}_2 - \text{S} - \text{Z}$$
$$\text{(CH}_3\text{)}_3\text{C}$$

wherein Z = straight or branched $C_{4-15}$ alkylene-COOR wherein the $C_{4-15}$ alkylene is tetramethylene, pentamethylene, hexamethylene, heptamethylene, octamethylene, nonamethylene, decamethylene, undecamethylene, dodecamethylene, tridecamethylene, tetradecamethylene, pentadecamethylene, 1,1-dimethylethylene, 2,2-dimethylethylene, 1-methyltrimethylene, 1-ethyltrimethylene, 2-methyltrimethylene, 2,2-dimethyltrimethylene, 1-methyltetramethylene, 2-methyltetramethylene, 2,2-dimethylhexamethylene, 1-methylheptamethylene, 2-methylheptamethylene, 2,2-dimethylheptamethylene, 1-methyloctamethylene, 2-methyloctamethylene, 2,2-dimethyloctamethylene, 2-methylnonamethylene or 2,2-dimethylnonamethylene, straight or branched $C_{2-15}$ alkenylene-COOR, straight or branched $$C_{1-15} \text{ alkylene} - C_6H_4 - COOR$$

or straight or branched $$C_{1-15} \text{ alkylene} - C_6H_4 - \text{straight}$$

or branched $C_{15}$ alkylene-COOR, and wherein R = H or a protective group for carboxyl or salts thereof.

2. The compound according to claim 1 wherein Z is —Y—COOR wherein Y is tetramethylene, pentamethylene, hexamethylene, decamethylene, undecamethylene, vinylene, 1,3-pentadiene-1,5-diyl, 1-propene-1,3-diyl or $$-CH_2 - C_6H_4 -.$$

3. The phenolic thioether according to claim 1, which is 5-(3,5-di-tert-butyl-4-hydroxyphenylthio)pentanoic acid.

4. The phenolic thioether according to claim 1, which is 3,5-di-tert-butyl-4-hydroxyphenylthio($C_2$-$C_{15}$)-alkenoic acid.

5. The phenolic thioether according to claim 1, which is 3,5-di-tert-butyl-4-hydroxyphenylthio($C_1$-$C_{15}$)alkylbenzoic acid.

6. A pharmaceutical composition for prevention or treatment of arteriosclerosis, which comprises an effective amount of the phenolic thioether or its salt according to claim 1 as the active ingredient, and a pharmaceutically acceptable inert carrier or diluent.

7. A method for prevention or treatment of arteriosclerosis, which comprises applying an effective amount of the phenolic thioether or its salt according to claim 1 to a patient of arteriosclerosis.

8. 6-(3,5-di-tert-butyl-4-hydroxyphenylthio)hexanoic acid.

9. 7-(3,5-di-tert-butyl-4-hydroxyphenylthio)heptanoic acid.

10. 11-(3,5-di-tert-butyl-4-hydroxyphenylthio)undecanoic acid.

11. 12-(3,5-di-tert-butyl-4-hydroxyphenylthio)dodecanoic acid.

12. 3-(3,5-di-tert-butyl-4-hydroxyphenylthio)acrylic acid.

13. 6-(3,5-di-tert-butyl-4-hydroxyphenylthio)-2,4-hexadienoic acid.

14. 4-(3,5-di-tert-butyl-4-hydroxyphenylthio)crotonic acid.

15. alpha-(3,5-di-tert-butyl-4-hydroxyphenylthio)-p-toluic acid.

* * * * *